(12) United States Patent
Mano

(10) Patent No.: US 10,384,108 B2
(45) Date of Patent: Aug. 20, 2019

(54) VEHICLE OPERATION ANALYSIS SYSTEM

(71) Applicant: KODEN Techno Info K.K., Tokyo (JP)

(72) Inventor: Hiroshi Mano, Tokyo (JP)

(73) Assignee: KODEN TECHNO INFO K.K., Tokyo (JP)

( * ) Notice: Subject to any disclaimer, the term of this patent is extended or adjusted under 35 U.S.C. 154(b) by 253 days.

(21) Appl. No.: 15/313,793

(22) PCT Filed: Oct. 21, 2015

(86) PCT No.: PCT/JP2015/079740
§ 371 (c)(1),
(2) Date: Nov. 23, 2016

(87) PCT Pub. No.: WO2016/068001
PCT Pub. Date: May 6, 2016

(65) Prior Publication Data
US 2017/0197129 A1 Jul. 13, 2017

(30) Foreign Application Priority Data

Oct. 31, 2014 (JP) .................................. 2014-222616

(51) Int. Cl.
*A63B 69/00* (2006.01)
*A61B 5/11* (2006.01)
*A63B 24/00* (2006.01)

(52) U.S. Cl.
CPC ............... *A63B 69/00* (2013.01); *A61B 5/11* (2013.01); *A63B 24/0006* (2013.01);
(Continued)

(58) Field of Classification Search
CPC .................................................... A63B 69/00
(Continued)

(56) References Cited

U.S. PATENT DOCUMENTS

2006/0000420 A1    1/2006   Martin Davies

FOREIGN PATENT DOCUMENTS

| GB | 2434517 A | 8/2007 |
| GB | 2452538 A | 3/2009 |

(Continued)

OTHER PUBLICATIONS

Nerino et al; "WBSN for the Assessment of the Hippotherapy: A Case Study"; 2011 International Conference on Body Sensor Networks (BSN); May 23, 2011; p. 101-106.

(Continued)

*Primary Examiner* — Kesha Frisby
(74) *Attorney, Agent, or Firm* — Oliff PLC

(57) ABSTRACT

A vehicle operation analysis system according to an embodiment of the present invention comprises: a first acceleration sensor configured attachable to an animal which is an object-to-be-operated operated by an operator, the first acceleration sensor measuring acceleration of the object-to-be-operated and outputting first acceleration data; a first communication device configured attachable to the object-to-be-operated, the first communication device being inputted with the first acceleration data from the first acceleration sensor and transmitting the first acceleration data; a second communication device configured attachable to the operator, the second communication device receiving the first acceleration data from the first communication device and outputting the first acceleration data; a second acceleration sensor measuring acceleration of the operator and outputting second acceleration data; and a calculation processing device that compares postures of the operator and the object-to-be-operated based on the first acceleration data and the second acceleration data.

18 Claims, 4 Drawing Sheets

(52) U.S. Cl.
CPC ... *A61B 2503/40* (2013.01); *A61B 2562/0219* (2013.01); *A63B 2220/40* (2013.01); *A63B 2225/50* (2013.01)

(58) Field of Classification Search
USPC ........................................................ 434/255
See application file for complete search history.

(56) References Cited

FOREIGN PATENT DOCUMENTS

| | | | |
|---|---|---|---|
| JP | 2004-344468 | A | 12/2004 |
| JP | 2008-500046 | A | 1/2008 |
| JP | 2008-272163 | A | 11/2008 |
| WO | 2005/115242 | A2 | 12/2005 |
| WO | 2006/053290 | A2 | 5/2006 |
| WO | 2009/040949 | A1 | 4/2009 |

OTHER PUBLICATIONS

May 28, 2018 Search Report issued in European Patent Application No. 15855697.7.
Nov. 17, 2016 International Search Report issued in International Patent Application No. PCT/JP2015/079740.

VEHICLE OPERATION ANALYSIS SYSTEM

TECHNICAL FIELD

The present invention relates to a vehicle operation analysis system.

BACKGROUND ART

Conventionally, a movement analysis system has been introduced at a scene of training of a sport, or the like. In the movement analysis system, a sensor is attached to a performer-of-an-action and an action state is measured and analyzed in order to increase an effect of the training. Furthermore, in recent years, by the appearance of a low-cost system combining an activity meter and a smart phone, this kind of movement analysis system has generally become widely used.

However, these movement analysis systems generally have the sensor attached only to the performer-of-the-action, and in this case, it is only possible for an analysis based only on action of the performer-of-the-action themselves to be made. Therefore, it becomes a problem that a sufficiently appropriate analysis cannot be made for an action where an operator operates a vehicle (object-to-be-operated), such as horse riding or cycling.

CITATION LIST

Patent Literature

PTL 1: JP 2004-344468 A

SUMMARY OF INVENTION

Technical Problem

The present invention was made in view of the above points, and has an object of providing a vehicle operation analysis system that, by measuring action states of an operator and an object-to-be-operated, makes possible appropriate action analysis of vehicle operation.

Solution to Problem

A vehicle operation analysis system according to an embodiment of the present invention comprises: a first acceleration sensor configured attachable to an animal which is an object-to-be-operated operated by an operator, the first acceleration sensor measuring acceleration of the object-to-be-operated and outputting first acceleration data; a first communication device configured attachable to the object-to-be-operated, the first communication device being inputted with the first acceleration data from the first acceleration sensor and transmitting the first acceleration data; a second communication device configured attachable to the operator, the second communication device receiving the first acceleration data from the first communication device and outputting the first acceleration data; a second acceleration sensor measuring acceleration of the operator and outputting second acceleration data; and a calculation processing device that compares postures of the operator and the object-to-be-operated based on the first acceleration data and the second acceleration data.

Advantageous Effects of Invention

The present invention makes it possible to provide a vehicle operation analysis system that, by measuring action states of an operator and an object-to-be-operated, makes possible appropriate action analysis of vehicle operation.

DESCRIPTION OF EMBODIMENTS

First, an outline of a vehicle operation analysis system according to an embodiment of the present invention will be described. Now, although hereafter description is made mainly on the premise of horse riding movement, it should be noted that the vehicle operation analysis system according to the present embodiment can be applied to any movement provided it is a movement in which an operator operates an object-to-be-operated, such as cycling, driving of a motorcycle/automobile, surfing, or skiing, for example.

Figure 1:
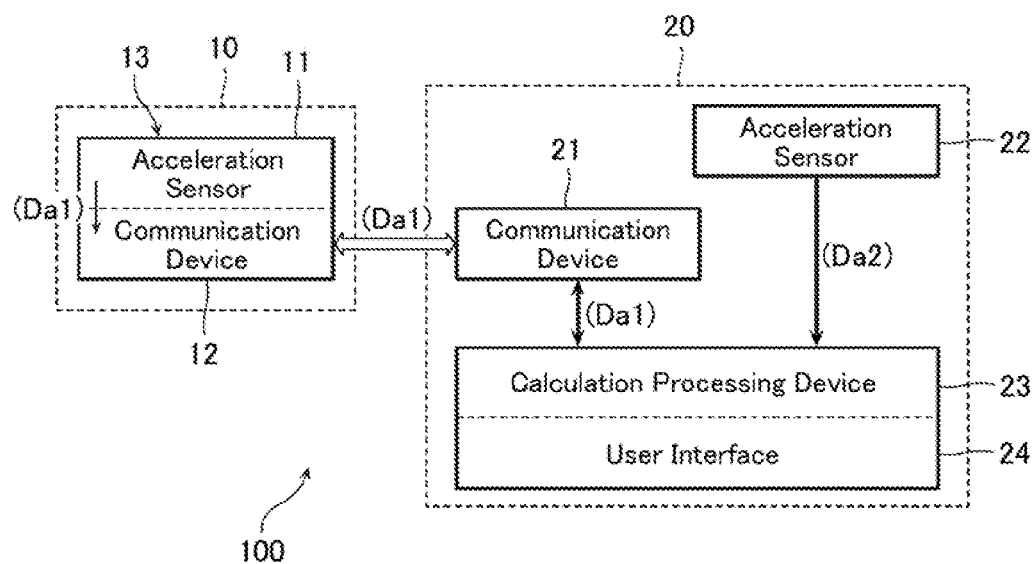
FIG. 1 is a view showing an outline of a vehicle operation analysis system according to an embodiment of the present invention.

FIG. 1 is a view showing the outline of the vehicle operation analysis system according to the present embodiment.

A vehicle operation analysis system 100 comprises an acceleration sensor 11 and a communication device 12 that are attachable to a horse which is an object-to-be-operated 10. The acceleration sensor 11 measures acceleration data Da1 accompanying action of the horse and outputs the acceleration data Da1 to the communication device 12. The communication device 12 is inputted with the acceleration data Da1 outputted from the acceleration sensor 11 and transmits the acceleration data Da1. The acceleration sensor 11 and the communication device 12 are, for example, packaged in one small-sized sensor terminal device 13 and attached to the likes of a saddle of the horse.

In addition, the vehicle operation analysis system 100 comprises a communication device 21, an acceleration sensor 22, a calculation processing device 23, and a user interface 24 that are attachable to a rider who is an operator. The communication device 21, by communication with the communication device 12, receives the acceleration data Da1 transmitted from the communication device 12 and outputs the acceleration data Da1 to the calculation processing device 23. Now, a variety of communication standards, such as Wi-Fi (registered trademark) or Bluetooth (registered trademark), can be employed in communication between the communication devices 12 and 21. The acceleration sensor 22 measures acceleration data Da2 accompanying action of the rider and outputs the acceleration data Da2 to the calculation processing device 22. The calculation processing device 23 collects the acceleration data Da1 of the horse and the acceleration data Da2 of the rider, and analyses to-and-fro movements and postures of the rider and the horse based on these acceleration data Da1 and Da2, thereby making a comparative evaluation. The user interface 24 enables operation of the vehicle operation analysis system 100 by a user and inspection of an analysis result due to the calculation processing device 23.

For example, in the case of a vehicle operation analysis system in which an acceleration sensor is attached only to the operator, action is analyzed using only acceleration data of the operator. In this case, an effect that the operator receives from the object-to-be-operated is not sufficiently reflected in the analysis result, hence judgement of whether the operator is making appropriate action matched to action of the object-to-be-operated is difficult. In that respect, as a result of the vehicle operation analysis system 100 according to the present embodiment, an acceleration sensor is attached not only to the operator but also to the object-to-be-operated, and to-and-fro movements and postures of both are analyzed, whereby a comparative evaluation is made. Therefore, the user can more accurately and easily achieve an understanding of whether action of the operator is matching action of the object-to-be-operated. In this respect, the vehicle operation analysis system 100 according to the present embodiment is particularly useful in the case of movement where the object-to-be-operated acts autonomously as in horse riding movement.

From here, application examples of the previously mentioned vehicle operation analysis system 100 will be listed and described.

FIGS. 2 to 6 are views showing application examples of the vehicle operation analysis system according to the present embodiment. Note that in FIGS. 2 to 6, configurations corresponding to the configurations shown in FIG. 1 are assigned with the same symbols as those assigned in FIG. 1.

Figure 2:
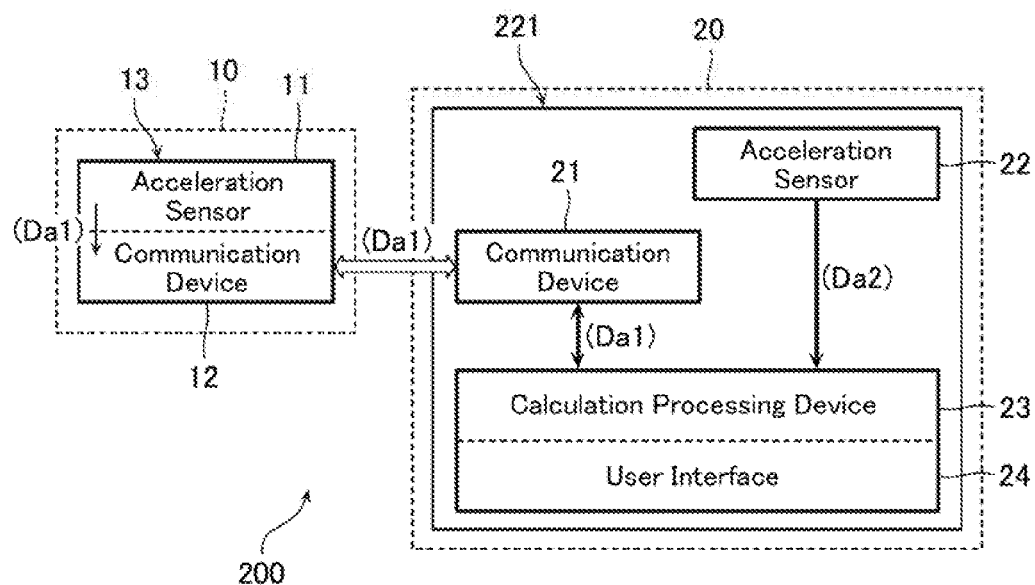
FIG. 2 is a view showing an application example of the vehicle operation analysis system according to the present embodiment.

A vehicle operation analysis system 200 shown in FIG. 2 is an example where the communication device 21, the acceleration sensor 22, the calculation processing device 23, and the user interface 24 attached to the operator 20 are mounted in one operation terminal device 22120. For example, if the user owns a smart phone having a communication function such as Wi-Fi or Bluetooth, an acceleration sensor, a calculation processing device, and a user interface employing the likes of a touch panel, then this smart phone may also be made use of as the operation terminal device 221.

In other words, as a result of the vehicle operation analysis system 200, in the case of a user having a smart phone, only the acceleration sensor 11 and the communication device 12 that are attached to the horse need be separately prepared, hence the vehicle operation analysis system 200 can be introduced easily and at low cost.

Figure 3:
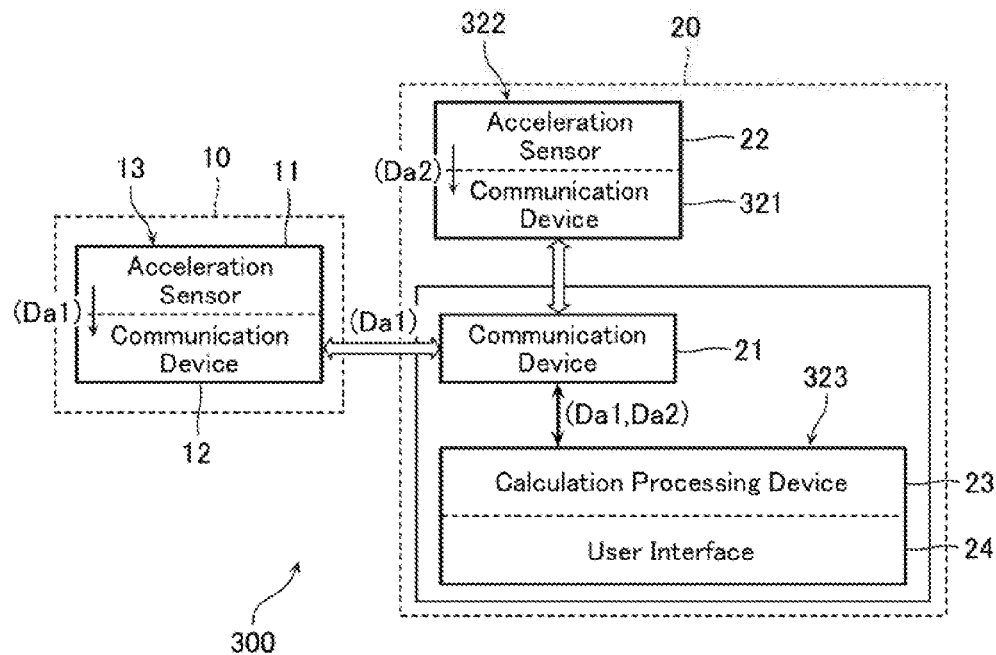
FIG. 3 is a view showing an application example of the vehicle operation analysis system according to the present embodiment.

A vehicle operation analysis system 300 shown in FIG. 3 is an example where the acceleration sensor 22 attached to the rider is configured as a separate terminal from the calculation processing device 23, and so on. The vehicle operation analysis system 300, in addition to comprising the configurations of the vehicle operation analysis system 100, comprises also a communication device 321 that is inputted with the acceleration data Da2 outputted from the acceleration sensor 22 and transmits the acceleration data Da2 to the communication device 21. In this case, the communication device 21 receives the acceleration data Da2 transmitted from the communication device 321, and then outputs this acceleration data Da2 along with the acceleration data Da1 to the calculation processing device 23. Note that the acceleration sensor 22 and the communication device 321 may be packaged in one small-sized sensor terminal device 322. Moreover, a variety of communication standards, such as Wi-Fi or Bluetooth, can be employed in communication between the communication devices 21 and 23.

As a result of this vehicle operation analysis system 300, the acceleration sensor 22 is separated from the likes of the calculation processing device 23, whereby the terminal including the acceleration sensor 22 can be miniaturized. In this case, a selection range of a place of attachment of the acceleration sensor 22 broadens more compared to in the case of the vehicle operation analysis system 200, hence it becomes possible to obtain more accurate acceleration data of the operator 20.

Figure 4:
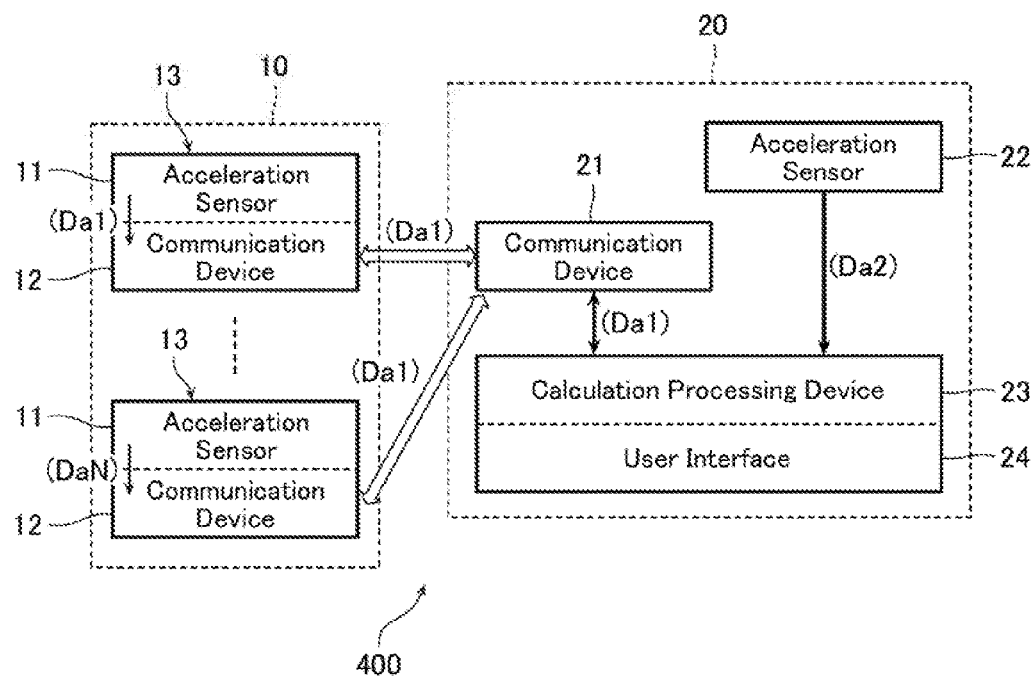
FIG. 4 is a view showing an application example of the vehicle operation analysis system according to the present embodiment.

A vehicle operation analysis system 400 shown in FIG. 4 is an example comprising a plurality of pairs of the acceleration sensor 11 and the communication device 12 attached to the horse. A plurality of the acceleration data Da1 outputted from the plurality of acceleration sensors 11 are collected in the communication device 21, via the communication devices 12, and outputted to the calculation processing device 23. Note that each of the pairs of the acceleration sensor 11 and the communication device 12 may be packaged in one small-sized sensor terminal device 13. Moreover, a variety of communication standards can be employed in communication between the communication device 21 and each of the communication devices 12. Particularly, if a wireless communication standard such as Wi-Fi or Bluetooth is employed, then there is no need to arrange an increase in wiring lines between the communication devices 12 and 21 even if the sensor terminal devices 13 increase, hence the vehicle operation analysis system 400 can be made physically simple.

As a result of this vehicle operation analysis system 400, a plurality of the acceleration sensors 11 can be attached to the object-to-be-operated 10, hence to-and-fro movement and posture of the object-to-be-operated 20 can be more accurately analyzed compared to in the case of the vehicle operation analysis system 100.

Figure 5:
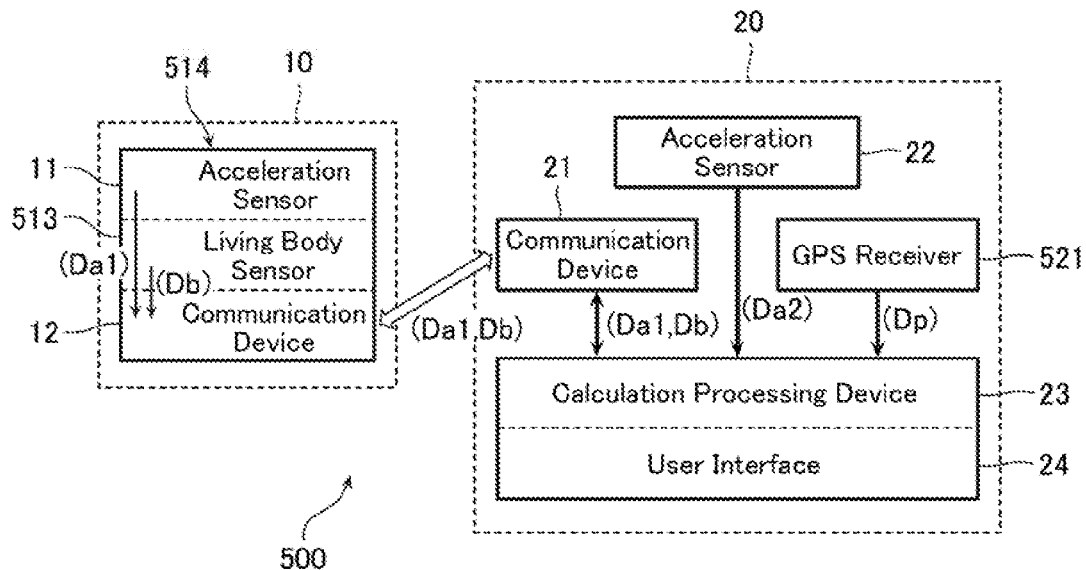
FIG. 5 is a view showing an application example of the vehicle operation analysis system according to the present embodiment.

A vehicle operation analysis system 500 shown in FIG. 5 is an example where a sensor other than the acceleration sensors 11 and 22 is attached to the object-to-be-operated 10 and the operator 20. The vehicle operation analysis system 500, in addition to comprising the configurations of the vehicle operation analysis system 100, comprises also: a living body sensor 513 configured attachable to an animal such as a horse which is the object-to-be-operated 10; and a GPS receiver 521 (positioning system receiver) configured attachable to the operator 20. The living body sensor 513 measures living body information of the animal, for example, its heart rate or body temperature, and outputs this living body information to the communication device 12 as living body data Db. In this case, the communication device 12, after being inputted with the living body data Db outputted from the living body sensor 513, transmits this living body data Db along with the acceleration data Da1 to the communication device 21. The communication device 21 receives the acceleration data Da1 and the living body data Db transmitted from the communication device 12 and outputs the acceleration data Da1 and the living body data Db to the calculation processing device 23. Then, this living body data Db, along with the acceleration data Db1, can be utilized in action analysis of the animal by the calculation processing device 23. As a result, not only does it become possible for the user to understand action of the animal 20 by utilization of the acceleration data Da1, it becomes possible for the user to understand also a state of the animal 20 at that time. Note that the GPS receiver 521 measures a position of the operator 20 and outputs position data Dp to the calculation processing device 23. This position data Dp, along with the acceleration data Db2, can be utilized in action analysis of the operator 20 by the calculation processing device 23. As a result, not only does it become possible for the user to understand action of the operator 20 by utilization of the acceleration data Da2, it becomes possible for the user to track the position of the operator 20 at that time. Note that a receiver of another positioning system such as GLONASS or Galileo may be employed instead of the GPS receiver 521.

Employing a sensor other than the acceleration sensors 11 and 22 as in this vehicle operation analysis system 500 makes it possible to analyze also an effect exerted on action by the likes of circumstances at a time of movement of the object-to-be-operated 10 and the operator 20.

Figure 6:
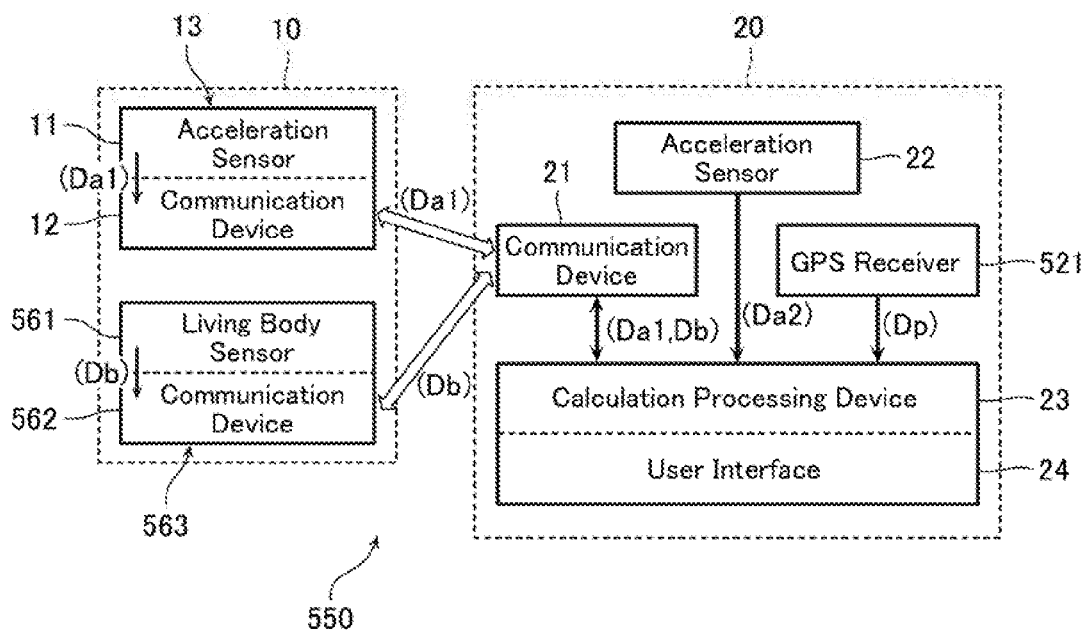
FIG. 6 is a view showing an application example of the vehicle operation analysis system according to the present embodiment.

Note that although in the vehicle operation analysis system 500, the living body sensor 513 is packaged along with the acceleration sensor 11 and the communication device 12 in one small-sized sensor terminal device 514, it is also possible, as in the vehicle operation analysis system 550 shown in FIG. 6, for a living body sensor 561 and a communication device 562 to be packaged in one small-sized sensor terminal device 563 and for the sensor terminal device 13 including the acceleration sensor 11 to be configured as a separate body. In this case, the living body sensor 561 (sensor terminal device 563) can be attached to any position of the object-to-be-operated 10, regardless of a position of the acceleration sensor 11 (sensor terminal device 13).

Figure 7:
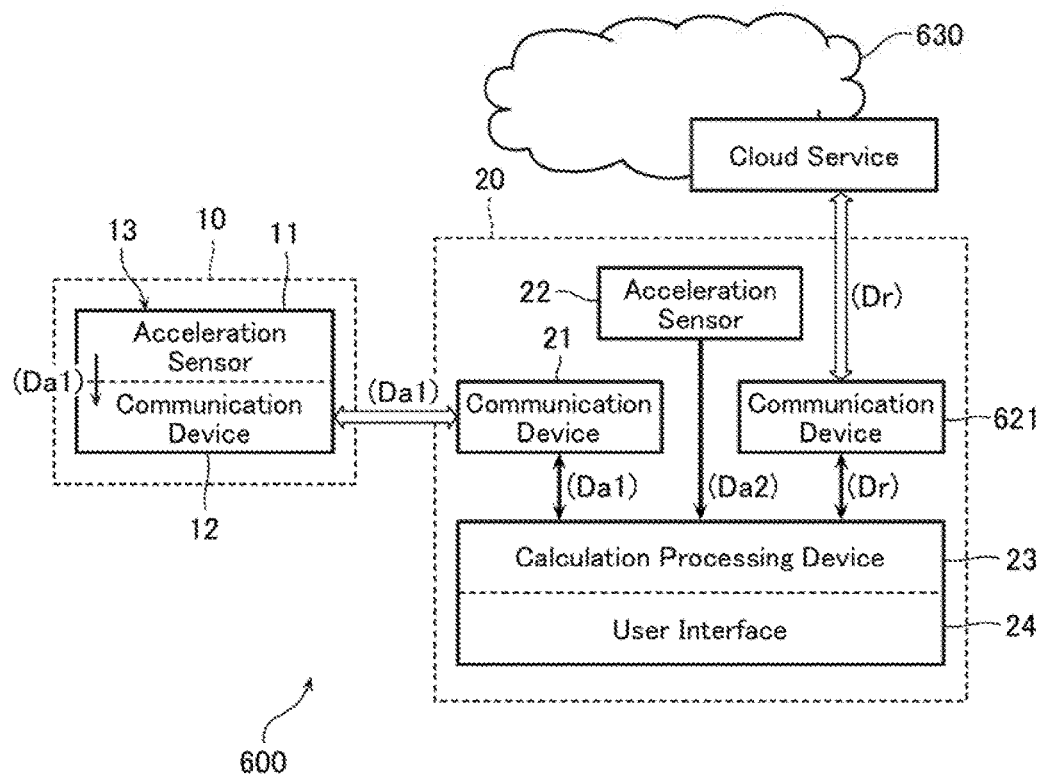
FIG. 7 is a view showing an application example of the vehicle operation analysis system according to the present embodiment.

A vehicle operation analysis system 600 shown in FIG. 7 is an example utilizing a cloud service. The vehicle operation analysis system 600, in addition to comprising the configurations of the vehicle operation analysis system 100, comprises also a communication device 621 that is inputted with an analysis result Dr generated by the calculation processing device 23 and transmits the analysis result Dr to a cloud server 630. In the case of this vehicle operation analysis system 600, analysis results generated by the calculation processing device 23 are accumulated in the cloud server 630. Note that when using the communication device 621 of a mobile phone, a variety of communication standards of a mobile phone, such as W-CDMA or LTE, can be employed in communication between the communication device 621 and the cloud server 630.

This vehicle operation analysis system 600 makes it possible for the user to be provided with various cloud services such as backup of analysis results or higher level analytical processing unable to be processed by the calculation processing device 23.

Other

Note that thus far examples of an embodiment of the invention have been described, but the present invention is not limited to these examples, and various changes, additions, and so on, are possible within a range not departing from the spirit of the invention.

REFERENCE SIGNS LIST

10 . . . object-to-be-operated
11, 22 . . . acceleration sensor
12, 21, 321, 562, 621 . . . communication device
13, 322, 514, 563 . . . sensor terminal device
20 . . . operator
23 . . . calculation processing device
24 . . . user interface
100, 200, 300, 400, 550, 500, 600 . . . vehicle operation analysis system
221, 323 . . . operation terminal device
513, 561 . . . living body sensor
521 . . . GPS receiver
630 . . . cloud server

The invention claimed is:

1. A vehicle operation analysis system, comprising:
a first acceleration sensor configured to be attached to an animal which is an object-to-be-operated operated by an operator, the first acceleration sensor measuring acceleration of the object-to-be-operated and outputting first acceleration data;
a living body sensor configured to be attached to the object-to-be-operated, the living body sensor measuring living body information of the object-to-be-operated and outputting living body data;
a second acceleration sensor configured to be attached to the operator, the second acceleration sensor measuring acceleration of the operator and outputting second acceleration data;
a first communication device configured to be attached to the object-to-be-operated, the first communication device being inputted with the first acceleration data from the first acceleration sensor and transmitting the first acceleration data;
a second communication device configured to be attached to the object-to-be-operated, the second communication device being inputted with the living body data from the living body sensor and transmitting the living body data;
a third communication device configured to be attached to the operator, the third communication device receiving the first acceleration data and the living body data from the first communication device and the second communication device and outputting the first acceleration data and the living body data;
a calculation processing device configured to be attached to the operator that compares postures of the operator and the object-to-be-operated based on the first acceleration data and the second acceleration data and analyzes a state of the object-to-be-operated based on the living body data; and
a user interface configured to be attached to the operator to enable operation of the vehicle operation analysis system by the operator and inspection of an analysis result due to the calculation processing device.

2. A vehicle operation analysis system comprising:
a first acceleration sensor configured to be attached to an animal which is an object-to-be-operated operated by an operator, the first acceleration sensor measuring acceleration of the object-to-be-operated and outputting first acceleration data;
a living body sensor configured to be attached to the object-to-be-operated, the living body sensor measuring living body information of the object-to-be-operated and outputting living body data;
a second acceleration sensor configured to be attached to the operator, the second acceleration sensor measuring acceleration of the operator and outputting second acceleration data;
a first communication device configured to be attached to the object-to-be-operated, the first communication device being inputted with the first acceleration data from the first acceleration sensor and transmitting the first acceleration data;
a second communication device configured to be attached to the object-to-be-operated, the second communication device being inputted with the living body data from the living body sensor and transmitting the living body data;
a third communication device configured to be attached to the operator, the third communication device receiving the first acceleration data and the living body data from the first communication device and the second communication device and outputting the first acceleration data and the living body data;
a calculation processing device configured to be attached to the operator that compares postures of the operator and the object-to-be-operated based on the first acceleration data and the second acceleration data and analyzes a state of the object-to-be-operated based on the living body data; and
a user interface configured to be attached to the operator to enable operation of the vehicle operation analysis system by the operator and inspection of an analysis result due to the calculation processing device,
wherein the second communication device is identical to the first communication device, and the first acceleration sensor, the living body sensor, and the first communication device are mounted in an identical first operation terminal configured to be attached to the object-to-be-operated.

3. A vehicle operation analysis system comprising:
a first acceleration sensor configured to be attached to an animal which is an object-to-be-operated operated by an operator, the first acceleration sensor measuring acceleration of the object-to-be-operated and outputting first acceleration data;
a living body sensor configured to be attached to the object-to-be-operated, the living body sensor measuring living body information of the object-to-be-operated and outputting living body data;
a second acceleration sensor configured to be attached to the operator, the second acceleration sensor measuring acceleration of the operator and outputting second acceleration data;
a first communication device configured to be attached to the object-to-be-operated, the first communication device being inputted with the first acceleration data from the first acceleration sensor and transmitting the first acceleration data;
a second communication device configured to be attached to the object-to-be-operated, the second communication device being inputted with the living body data from the living body sensor and transmitting the living body data;
a third communication device configured to be attached to the operator, the third communication device receiving the first acceleration data and the living body data from the first communication device and the second communication device and outputting the first acceleration data and the living body data;
a calculation processing device configured to be attached to the operator that compares postures of the operator and the object-to-be-operated based on the first acceleration data and the second acceleration data and analyzes a state of the object-to-be-operated based on the living body data; and
a user interface configured to be attached to the operator to enable operation of the vehicle operation analysis system by the operator and inspection of an analysis result due to the calculation processing device,
wherein:
the first acceleration sensor and the first communication device are mounted in an identical first operation terminal configured to be attached to the object-to-be-operated,
the living body sensor and the second communication device are mounted in an identical second operation terminal configured to be attached to the object-to-be-operated, and
the second operation terminal is different from the first operation terminal.

4. The vehicle operation analysis system according to claim 1, wherein the second acceleration sensor, the third communication device, and the calculation processing device are mounted in an identical first operation terminal configured to be attached to the operator.

5. The vehicle operation analysis system according to claim 1, further comprising a fourth communication device configured to be attached to the operator, the fourth communication device being inputted with the second acceleration data from the second acceleration sensor and transmitting the second acceleration data, wherein
the third communication device receives the second acceleration data from the fourth communication device and outputs the second acceleration data to the calculation processing device.

6. The vehicle operation analysis system according to claim 1, comprising a plurality of pairs of the first acceleration sensor and the first communication device.

7. The vehicle operation analysis system according to claim 1, further comprising a satellite positioning system receiver configured to be attached to the operator, the satellite positioning system receiver measuring a position of the operator and outputting position data, wherein the calculation processing device tracks the position of the operator based on the position data.

8. The vehicle operation analysis system according to claim 1, further comprising a fifth communication device configured to be attached to the operator, the fifth communication device being inputted with an analysis result generated by the calculation processing device and transmitting the analysis result to a server of a cloud service.

9. The vehicle operation analysis system according to claim 2, wherein the second acceleration sensor, the third communication device, and the calculation processing device are mounted in an identical second operation terminal configured to be attached to the operator.

10. The vehicle operation analysis system according to claim 2, further comprising a fourth communication device configured to be attached to the operator, the fourth communication device being inputted with the second acceleration data from the second acceleration sensor and transmitting the second acceleration data, wherein the third communication device receives the second acceleration data from the fourth communication device and outputs the second acceleration data to the calculation processing device.

11. The vehicle operation analysis system according to claim 2, comprising a plurality of pairs of the first acceleration sensor and the first communication device.

12. The vehicle operation analysis system according to claim 2, further comprising a satellite positioning system receiver configured to be attached to the operator, the satellite positioning system receiver measuring a position of the operator and outputting position data, wherein the calculation processing device tracks the position of the operator based on the position data.

13. The vehicle operation analysis system according to claim 2, further comprising a fifth communication device configured to be attached to the operator, the fifth communication device being inputted with an analysis result generated by the calculation processing device and transmitting the analysis result to a server of a cloud service.

14. The vehicle operation analysis system according to claim 3, wherein the second acceleration sensor, the third communication device, and the calculation processing device are mounted in an identical third operation terminal configured to be attached to the operator.

15. The vehicle operation analysis system according to claim 3, further comprising a fourth communication device configured to be attached to the operator, the fourth communication device being inputted with the second acceleration data from the second acceleration sensor and transmitting the second acceleration data, wherein the third communication device receives the second acceleration data from the fourth communication device and outputs the second acceleration data to the calculation processing device.

16. The vehicle operation analysis system according to claim 3, comprising a plurality of pairs of the first acceleration sensor and the first communication device.

17. The vehicle operation analysis system according to claim 3, further comprising a satellite positioning system receiver configured to be attached to the operator, the satellite positioning system receiver measuring a position of the operator and outputting position data, wherein the calculation processing device tracks the position of the operator based on the position data.

18. The vehicle operation analysis system according to claim 3, further comprising a fifth communication device configured to be attached to the operator, the fifth communication device being inputted with an analysis result generated by the calculation processing device and transmitting the analysis result to a server of a cloud service.

* * * * *